(12) United States Patent
Maeda et al.

(10) Patent No.: US 6,224,658 B1
(45) Date of Patent: May 1, 2001

(54) *THIOBACILLUS THIOOXIDANS* GROWTH INHIBITOR, CEMENT COMPOSITION, AND CEMENT STRUCTURE (75) Inventors: Terunobu Maeda, Ibaraki-ken; Atsunori Negishi, Tsukuba; Hiromi Uchida, Tokyo; Toshio Enokida, Tsukuba; Reiko Tanaka, Tokyo, all of (JP)

(73) Assignee: Hazama Corporation, Tokyo (JP)

( * ) Notice: Subject to any disclaimer, the term of this patent is extended or adjusted under 35 U.S.C. 154(b) by 0 days.

(21) Appl. No.: 09/269,147

(22) PCT Filed: Jul. 14, 1998

(86) PCT No.: PCT/JP98/03147

§ 371 Date: Mar. 12, 1999

§ 102(e) Date: Mar. 12, 1999

(87) PCT Pub. No.: WO99/03349

PCT Pub. Date: Jan. 28, 1999

(30) Foreign Application Priority Data

Jul. 14, 1997  (JP) .................................... 9-188686

(51) Int. Cl.[7] .......................... A01N 59/16; A01N 25/00; C04B 22/08; C04B 22/12
(52) U.S. Cl. ....................... 106/18.32; 106/727; 106/808; 106/823; 424/617; 514/185
(58) Field of Search ................................ 106/18.32, 727, 106/808, 819, 823; 424/617; 514/185

(56) References Cited

FOREIGN PATENT DOCUMENTS

| | | |
|---|---|---|
| 881 198 | * 12/1998 | (EP) . |
| 882 398 | * 12/1998 | (EP) . |
| 4-149053 | 5/1992 | (JP) . |
| 6-72815 | 3/1994 | (JP) . |
| 10-25142 | 1/1998 | (JP) . |
| 97/30005 | * 8/1997 | (WO) . |
| 98/114062 | * 4/1998 | (WO) . |

OTHER PUBLICATIONS

Chemical Abstract No. 130:70263, abstract of Japanese Patent Specification No. 10–316461, Dec. 1998.*

Chemical Abstract No. 130:84999, abstract of Japanese Patent Specification No. 10–316462, Dec. 1998.*

* cited by examiner

*Primary Examiner*—Anthony Green
(74) *Attorney, Agent, or Firm*—Darby & Darby (57) ABSTRACT

To provide a *Thiobacillus thiooxidans* growth inhibitor, a cement composition, and a cement structure which are capable of inhibiting effectively growth of *Thiobacillus thiooxidans* not only in the neutral pH range but also in the acidic pH range of 4 or below, of which active component metal ions are sufficiently prevented from being dissolved and released when contained in a cement structure, and of which effect can be maintained for a prolonged period of time. The inhibitor contains a first component selected from the group consisting of nickel phthalocyanine powders, powders of a nickel phthalocyanine derivative, and mixtures thereof, and a second component selected from the group consisting of tungsten powders, powders of a substantially water-insoluble tungsten compound, a water-soluble salt of tungstic acid turning to substantially water-insoluble when reacted with cement, and mixtures thereof.

10 Claims, 3 Drawing Sheets

*THIOBACILLUS THIOOXIDANS* GROWTH INHIBITOR, CEMENT COMPOSITION, AND CEMENT STRUCTURE

FIELD OF ART

The present invention relates to a *Thiobacillus thiooxidans* growth inhibitor, a cement composition and a cement structure containing such growth inhibitor. In particular, the present invention relates to a growth inhibitor, a cement composition, and a cement structure which are capable of effectively inhibiting growth of *Thiobacillus thiooxidans* in its habitat, which can be used without causing environmental pollution even under acidic conditions, and which can be used for preventing deterioration of cement structures including a variety of concrete structures such as those in sewage treatment facilities, mortar structures, or concrete sewers that are brought into contact with sewage water.

BACKGROUND OF THE INVENTION

Cement structures such as concrete and mortar structures in sewage treatment facilities and the like conventionally have problems of becoming gypseous and deteriorated. This deterioration is ascribable to sulfur-oxidizing bacteria of the genus Thiobacillus that oxidize hydrogen sulfide to produce sulfuric acid. These bacteria usually live widely in soil or water, and grow by oxidation of sulfur compounds and assimilation of carbon dioxide. Some species of the sulfur-oxidizing bacteria of the genus Thiobacillus live in structures in contact with sewage water, yet some species of the bacteria live in structures exposed to the air and not in contact with sewage water in the sewage treatment facilities.

For preventing deterioration of such structures, various methods have hitherto been proposed. At present, practically employed methods include coating the structures with corrosion resisting materials. However, the coatings of the corrosion resisting materials are easily damaged from pinholes or scratches, and thus have problems in durability. In addition, it is difficult to coat the parts having complex configurations and fine parts such as joints of small-diameter tubes.

It is known that heavy metal ions could kill the sulfur-oxidizing bacteria of the genus Thiobacillus. Such bactericidal action is exhibited by direct action of heavy metal ions on the bacteria. Since heavy metals are dissolved and released in an ionized state, a large amount of heavy metals are required for achieving the bactericidal action. Released ions of some kinds of heavy metals have seriously harmful effect on environment, so that such metals cannot be used in sewage treatment facilities.

To overcome these problems, there is proposed and practiced a method for preventing deterioration of cement structures induced by sulfur-oxidizing bacteria of the genus Thiobacillus, wherein particular metals or metal oxides that are insoluble in water but soluble in sulfuric acid, such as nickel, are added to structures such as those of concrete (JP-A-4-149053). This method is excellent in that the particular metals completely prevent the sulfur-oxidizing activity, respiration, and carbon dioxide-fixation activity of the sulfur-oxidizing bacteria in the neutral pH range, resulting in sufficient prevention of deterioration of cement structures induced by sulfur-oxidizing bacteria.

However, inhibitory activities of nickel or its oxides against the bacteria of the genus Thiobacillus decrease toward the acidic pH range, and hardly exhibited at pH 3 or below. Therefore, the inhibitory activity of such metals can be maintained sufficiently in the area usually in contact with sewage water where the pH value is kept near neutrality, but hardly exhibited in acidic area not in direct contact with sewage water, or when sewage water is transiently acidified. In addition, when the metals that are insoluble in water but soluble in sulfuric acid, such as nickel, are exposed to strong acid, such metals are dissolved and released as metal ions, thus being unpreferable in the environmental point of view. The release of the metal ions also reduces the volume of the inhibitor itself, causing difficulty in maintaining the inhibitory activity against the bacteria of the genus Thiobacillus for a prolonged period of time.

Metals having inhibitory activities against the bacteria of the genus Thiobacillus other than nickel have also been under research. For example, it is known that a mixture of molybdenum, ammonium molybdate, or ammonium molybdate and tungsten activates growth of *Thiobacillus novellus,* whereas tungsten, when used alone, inhibits growth of the same bacteria (Journal of Bacteriology, Vol. 153, No. 2 (1983) William M. et al. "Sulfite Oxidase Activity in *Thiobacillus novellus*" p.941–944). It is also reported that molybdenum ($Mo^{4+}$), which is known to activate growth of the above-mentioned *Thiobacillus novellus,* inhibits growth of *Thiobacillus thiooxidans* (Chemical Abstracts, Vol. 95, No. 1 (Jul. 6, 1981) p127 (1081a)).

Thus, even the sulfur-oxidizing bacteria of the same genus of Thiobacillus have different growth inhibitory mechanism. Therefore, even if a certain growth inhibitor is demonstrated to have an effect on *Thiobacillus novellus* viable in the neutral pH range of 6 to 8, such an inhibitor will not be used in the acidic pH range of 2 to 6, where *Thiobacillus novellus* is hardly viable. Further, it is not believed that a substance that inhibits growth of *Thiobacillus novellus* equally inhibits growth of *Thiobacillus thiooxidans* viable in the pH range of 2 to 6. Recent researches therefore indicate that the growth inhibitors proposed hitherto are not effective to all species of the sulfur-oxidizing bacteria of the genus Thiobacillus.

DISCLOSURE OF THE INVENTION

It is an object of the present invention to provide a *Thiobacillus thiooxidans* growth inhibitor which is capable of inhibiting effectively growth of *Thiobacillus thiooxidans* not only in the neutral pH range but also in the acidic pH range of 4 or below for a prolonged period of time.

It is another object of the present invention to provide a *Thiobacillus thiooxidans* growth inhibitor which can be added to a concrete material containing cement, water, and aggregates, or to a mortar material, and easily dispersed therein by mixing.

It is yet another object of the present invention to provide the growth inhibitor which can be used as a material for a cement structure to effectively prevent deterioration thereof induced by *Thiobacillus thiooxidans,* and which has excellent dispersibility when mixed in a ready-mixed concrete.

It is still another object of the present invention to provide a cement structure such as those of concrete or mortar that is effectively prevented from undergoing deterioration induced by *Thiobacillus thiooxidans* for a prolonged period of time even, for example, in sewage treatment facilities or in potentially acidic areas, and a cement composition that facilitates preparation of such cement structure.

The present inventors have confirmed that the conventional growth inhibitors for sulfur-oxidizing bacteria of the genus Thiobacillus containing nickel as an active component are capable of fully exhibiting their effect in cement structures that are maintained in the neutral pH range by, for example, direct contact with sewage water. The inventors have, however, also confirmed that such nickel-containing growth inhibitors exhibit decreased or almost no growth inhibitory activity particularly against *Thiobacillus thiooxidans* when the structure is in proximity to sewage treatment facilities, and the structure surface is not in direct contact with sewage water and kept in the acidic pH range of 4 or below by the action of hydrogen sulfide in the atmosphere.

The reason for the difference in the growth inhibitory effect on the same bacteria depending on the pH in the environment is not known. However, the conventional nickel-containing growth inhibitors do not act directly on the bacteria per se, but bind to the enzymes of the bacteria to exhibit the growth inhibitory activity. It is believed that the inhibitors do not bind to the enzymes sufficiently in the acidic pH range, resulting in lowered growth inhibitory activity. In view of the above, the inventors have made intensive studies searching for inhibitors which are capable of exhibiting sufficient growth inhibitory activity against *Thiobacillus thiooxidans* living in the near neutral to acidic pH range of 2 to 6, not only around the neutral pH range, but also in the acidic pH range of 4 or below, and which are capable of maintaining their effect for a prolonged period of time without being dissolved and released as metal ions even under strongly acidic conditions. As a result, the inventors have found that the above problems can be solved by a combination of nickel phthalocyanine powders and/or powders of a nickel phthalocyanine derivative, and tungsten powders and/or powders of a substantially water-insoluble tungsten compound and/or a water-soluble salt of tungstic acid that turns to water-insoluble when reacted with cement, thereby completing the present invention.

Further, the inventors have also made an intensive study for giving the inhibiting ability of the *Thiobacillus thiooxidans* growth inhibitor to cement structures such as concrete or mortar structures more effectively. Consequently, they have found that this can be achieved by preparing in advance a water dispersion of the substantially water-insoluble powders in the inhibitors, in order to disperse the inhibitor easily in concrete or mortar materials, thereby completing the present invention.

Therefore, according to the present invention, there is provided a *Thiobacillus thiooxidans* growth inhibitor comprising a first component selected from the group consisting of nickel phthalocyanine powders, powders of a nickel phthalocyanine derivative, and mixtures thereof, and a second component selected from the group consisting of tungsten powders, powders of a substantially water-insoluble tungsten compound, a water-soluble salt of tungstic acid turning to substantially water-insoluble when reacted with cement, and mixtures thereof.

According to the present invention, there is also provided a *Thiobacillus thiooxidans* growth inhibitor comprising the aforementioned first component, the aforementioned second component, water, and a dispersant for dispersing water-insoluble powders in the first and second components in water, wherein said inhibitor is in a form of a water dispersion.

According to the present invention, there is further provided a cement composition comprising cement, aggregates, water, the aforementioned first component, the aforementioned second component, and a dispersant for dispersing water-insoluble powders in the first and second components, wherein said composition is in a fluidized state.

According to the present invention, there is also provided a cement structure obtained by hardening the aforementioned cement composition.

PREFERRED EMBODIMENT OF THE INVENTION

The present invention will now be explained in detail.

The inhibitor of the present invention, when mixed with a structural material such as concrete, mortar, or a polymer material for sewage treatment facilities and the like, acts to inhibit growth of *Thiobacillus thiooxidans*, which contributes to deterioration of such a structural material. The inhibitor acts effectively not only on structures in direct contact with sewage water, but also on structures near sewage treatment facilities under the conditions that the structure surface is in the acidic pH range of 4 or below by the action of hydrogen sulfide in the atmosphere, to thereby prevent deterioration of the structures effectively.

The inhibitor of the present invention contains as active components powders of particular metals that are hardly dissolved and released into sewage water or the like, and are hardly released as metal ions even under acidic conditions, when the inhibitor is contained in cement structures such as concrete or mortar structures. Accordingly, the inhibitory activity can be maintained for a prolonged period of time. The active components of the present invention, which, as metals per se and not in the form of metal ions, inhibit the growth of *Thiobacillus thiooxidans*, have little growth inhibitory activity against Gram-negative bacteria such as Escherichia coli or Gram-positive bacteria such as Staphylococcus aureus, and have little bactericidal effect even on *Thiobacillus thiooxidans*. The principle of such inhibitory effect has not been clarified. However, as mentioned above, it is believed that the active components do not act directly on *Thiobacillus thiooxidans* itself, but on the enzyme associated with the generation of sulfuric acid by the bacteria, to interrupt the generation of sulfuric acid, thereby exhibiting the growth inhibitory activity against *Thiobacillus thiooxidans*. Therefore, the effect of the active components of the present invention is clearly distinguished from that of the conventionally proposed heavy metal ions having bactericidal effect directly on a variety of bacteria.

The inhibitor of the present invention contains both of the first component selected from the group consisting of nickel phthalocyanine powders, powders of a nickel phthalocyanine derivative, and mixtures thereof, and the second component selected from the group consisting of tungsten powders, powders of a substantially water-insoluble tungsten compound, a water-soluble salt of tungstic acid turning to substantially water-insoluble when reacted with cement, and mixtures thereof.

The nickel phthalocyanine powders are powders of a compound having a phthalocyanine skeleton which has no substituent and to which a nickel atom is coordination-bonded. The nickel phthalocyanine powders are water-insoluble, and also substantially insoluble in acid.

The powders of a nickel phthalocyanine derivative are powders of a compound having a substitutional atom other than a hydrogen atom or a substitutional group in the benzene rings of the nickel phthalocyanine skeleton molecule. This compound is usually insoluble in water, and hardly soluble in acid. Examples of the substitutional atom or group in the nickel phthalocyanine derivative may include: halogen atoms such as fluorine, chlorine, bromine, or iodine; substituted or non-substituted alkyl groups such as a methyl, ethyl, propyl, butyl, sec-butyl, tert-butyl, pentyl, hexyl, heptyl, octyl, stearyl, trichloromethyl, cyclopropyl, 1,3-cyclohexadienyl, 2-cyclopenten-1-yl, or 2,4-cyclopentadiene-1-yldenyl group; substituted or non-substituted alkoxy groups such as methoxy, ethoxy, propoxy, n-butoxy, sec-butoxy, tert-butoxy, pentyloxy, hexyloxy, stearyloxy, or triphloromethoxy group; substituted or non-substituted thioalkoxy groups such as methylthio, ethylthio, propylthio, butylthio, sec-butylthio, tert-butylthio, pentylthio, hexylthio, heptylthio, or octylthio group; nitro, cyano, carbonyl, ester, hydroxyl, sulfonic, or vinyl group; alkyl-substituted amino groups such as methylamino, dimethylamino, ethyamino, diethylamino, dipropylamino, or dibutylamino group; carbocyclic aromatic amino groups such as diphenylamino or ditolylamino group; mono- or di-substituted amino groups such as bis(acetoxymethyl) amino, bis(acetoxyethyl) amino, bis(acetoxypropyl) amino, bis(acetoxybutyl) amino, or dibenzylamino group; substituted or non-substituted aryloxy groups such as phenoxy, p-tert-butylphenoxy, or 3-fluorophenoxy group; substituted or non-substituted arylthio groups such as phenylthio or 3-fluorophenylthio group; and substituted or non-substituted aromatic ring groups such as phenyl, biphenyl, triphenyl, tetraphenyl, 3-nitrophenyl, 4-methylthiophenyl, 3,5-dicyanophenyl, o-tolyl, m-tolyl, p-tolyl, xylyl, o-cumenyl, m-cumenyl, p-cumenyl, mesityl, pentalenyl, indenyl, naphthyl, azulenyl, heptalenyl, acenaphthylenyl, phenalenyl, fluorenyl, anthryl, anthraquinonyl, 3-methylanthryl, phenanthryl, triphenylene, pyrenyl, chrysenyl, 2-ethyl-1-chrysenyl, picenyl, perylenyl, 6-chloroperylenyl, pentaphenyl, pentacenyl, tetraphenylene, hexaphenyl, hexacenyl, rubicenyl, coronenyl, trinaphthylenyl, heptaphenyl, heptacenyl, pyranthrenyl, or ovalenyl group.

The first component exhibits growth inhibitory activity against Thiobacillus thiooxidans under the conditions around the neutral pH range. The average particle size of the first component is not particularly limited. The particle size may preferably be decided so that the powders exhibit the growth inhibitory effect when mixed in a cement structure such as a concrete or mortar structure, and are arranged at desired locations in the structure when molded. Specifically, the average particle size of the powders in the first component is preferably 0.01 $\mu$m to 1 mm, more preferably 1 $\mu$m to 0.1 mm.

In the second component, the tungsten powders are insoluble in water, and hardly soluble in acid. On the other hand, the powders of a tungsten compound are substantially water-insoluble, and preferably hardly soluble in acid. Examples of such tungsten compound may include, for example, tungstic acid such as $W_{28}O_{58}$ (commonly referred to as "blue oxide") or $WO_3$; tungstate such as calcium tungstate ($CaWO_4$); or mixtures thereof. As the second component, a water-soluble salt of tungstic acid that turns to substantially water-insoluble when reacted with cement may also be used. Examples of such salt of tungstic acid may include sodium tungstate ($Na_2WO_4$, $Na_2WO_9$). Since such salt of tungstic acid is water-soluble, it can easily be dispersed homogeneously in a concrete or mortar material. Further, when reacted with cement, a major part of the salt of tungstic acid turns to substantially water-insoluble calcium tungstate, so that it remains water-insoluble in the cement structure, and is hardly soluble in acid. Consequently, not the metal ions, but the metal per se inhibits the growth of Thiobacillus thiooxidans, and its effect can be maintained for a prolonged period of time.

The second component exhibits growth inhibitory activity against Thiobacillus thiooxidans under the acidic conditions, in particular in the acidic pH range of 4 or below. In the second component, the average particle size of the powders is not particularly limited. The particle size may preferably be decided so that the powders effectively exhibit the growth inhibitory effect when contained in a cement structure, and are arranged at desired locations in the structure when molded. Specifically, the average particle size of the powders in the second component is preferably 1 $\mu$m to 0.2 mm.

The inhibitor of the present invention may additionally contain other active components as long as the objects of the present invention are achieved. When only the first and second components are the active components, the effective concentration thereof is preferably not lower than 1 $\mu$mol/l, more preferably 10 to 100 $\mu$mol/l with respect to the habitat of Thiobacillus thiooxidans. For example, the present inhibitor is capable of exhibiting sufficient growth inhibitory effect on Thiobacillus thiooxidans even with the active components being in the amount of as small as 0.0001 to 1.0 parts by weight, preferably 0.0001 to 0.1 parts by weight based on 100 parts by weight of cement in the cement structure, to prevent the Thiobacillus thiooxidans—induced deterioration of a cement structure. Moreover, the effect of the inhibitor can be maintained for a remarkably longer time than that of the coatings of conventional corrosion resisting materials.

The mixing ratio of the first component to the second component is preferably 1:0.1–1.0 by weight.

The inhibitor of the present invention may contain water and a dispersant for dispersing water-insoluble powders in the first and second components in water, to be in the form of a water dispersion that is convenient for mixing in a cement composition such as concrete or mortar before hardening. In a preferable water dispersion, the first and second components are homogeneously dispersed or partially dissolved in water, and the dispersed state is maintained preferably for 60 days or longer at room temperature.

Examples of the dispersant may include admixtures such as high-performance water reducing agents or superplasticizers, or complexes thereof. Specifically, salts of naphthalenesulfonic acid, salts of melaminesulfonic acid, salts of ligninsulfonic acid, salts of polycarboxylic acid, polyol, hydroxy carboxylic acid, rhodan compounds, triazine-based compounds, and mixtures thereof may be used. Alternatively, commercially available admixtures for concrete may also be used as they are.

In the present inhibitor in the form of a water dispersion, the mixing ratio of water is preferably 50 to 1000 parts by weight, more preferably 100 to 300 parts by weight, and that of the dispersant is preferably 50 to 500 parts by weight, more preferably 100 to 500 parts by weight, based on 100 parts by weight of the first and second components together.

The present inhibitor in the form of a water dispersion may be prepared by dissolving the dispersant in water, dispersing or dissolving the second component therein by mixing, and then adding the first component little by little under agitation for dispersion.

The cement composition of the present invention contains cement, aggregates, water, the first component, the second component, and the dispersant for dispersing water-insoluble powders in the first and second components. The cement composition is in a fluidized state. Thus, the composition may conveniently be transported in a concrete mixer truck. Further, the first and second components are prevented from segregating from other components or aggregating, so that the present cement composition may be made into a cement structure by an ordinary method for placing readymixed concrete.

There is nor particular limitation on the cement, and a variety of cement such as Portland cement, blended cement, or special cement may be used.

The aggregates may be selected from a variety of coarse or fine aggregates. The particle size of the aggregates may suitably be selected depending on the structure to be produced.

The first and second components, and the dispersant may preferably be those discussed above.

In the cement composition of the present invention, the mixing ratio of the aggregates such as coarse and/or fine aggregates may preferably be selected from within the range of 50 to 500 parts by weight based on 100 parts by weight of cement, depending on the need. The mixing ratio of water may preferably be selected from within the range of 20 to 80 parts by weight based on 100 parts by weight of cement, depending on the need. The mixing ratio of the first component may preferably be selected from within the range of 0. 05 to 2 parts by weight based on 100 parts by weight of cement, depending on the need. The mixing ratio of the second component may preferably be selected from within the range of 0.05 to 2 parts by weight based on 100 parts by weight of cement, depending on the need. The mixing ratio of the dispersant may preferably be selected from within the range of 50 to 1000 parts by weight based on 100 parts by weight of the first and second components together, depending on the need.

A method of preparing the present cement composition is not particularly limited as long as the cement composition is in a fluidized state with each component being dispersed or partially dissolved therein. For example, the cement composition may be prepared by adding the inhibitor in the form of a water dispersion containing the first and second components, the dispersant, and water to a mixture of the cement, the aggregates, and water, followed by mixing.

The cement composition of the present invention may also contain a variety of other additives as desired as long as the objects of the present invention are achieved. Examples of such other additives may include air-entraining agents, water reducing agents, or superplasticizers, which are usually added in producing concrete or mortar structures. The mixing ratio of such other additives may suitably be decided depending on the structure to be produced.

The cement structure of the present invention is a concrete or mortar structure produced by hardening the cement composition.

The cement composition may be hardened by commonly known methods for placing and compaction, or for molding and curing. The molding and curing may be carried out by centrifugal molding method.

The conditions for hardening are not particularly limited, and may suitably be selected depending on the cement structure to be produced.

The cement structure of the present invention inhibits growth of *Thiobacillus thiooxidans,* and is prevented or inhibited from being deteriorated, with the first and second components contained therein being hardly dissolved and released in the form of metal ions. Accordingly, the present cement structure may effectively beused not only in places that are in direct contact with sewage water in sewage treatment facilities, but also in places that are not in contact with sewage water but are acidified on the surface.

The inhibitor of the present invention contains particular metal compounds, i.e., the first and second components. Thus, the present inhibitor sufficiently inhibits growth of *Thiobacillus thiooxidans* not only in the neutral pH range, but also in the acidic pH range of 4 or below. In addition, these components exhibit the growth inhibitory activity without being dissolved and released as metal ions from the cement structure, so that the effect of these components is maintained for a prolonged period of time. Accordingly, the present cement structure, that is, the cement structure such as a concrete or mortar structure containing a small amount of present inhibitor, for example in sewage treatment facilities, is capable of sufficiently inhibiting growth of *Thiobacillus thiooxidans* without substantial lowering in the strength of the structure.

The cement composition of the present invention is in a fluidized state wherein the active components of the inhibitor, the first and second components, are dispersed or partially dissolved. Accordingly, the present cement composition is useful for producing the cement structure of the present invention, and can be transported in a concrete mixer truck in a fluidized state without segregation.

EXAMPLES

The present invention will now be explained in detail with reference to Examples and Comparative Examples. However, the present invention is not limited to these.

Examples 1–2 and Comparative Examples 1–2

20 ml of thiosulfate-inorganic salt medium (pH 7.0) containing 0.2% sodium thiosulfate, 0.03% yeast extract, 0.3% $(NH_4)_2SO_4$, 0.05% $MgSO_4.7H_2O$, 0.05% $K_2HPO_4$, 0.01% KCl, and 0.001% $Ca(NO_3)_{2.4}H_2O$ was inoculated with 1.0 g of corroded concrete, and kept under aerobic conditions at 30° C. When the pH of the medium decreased to 2.0, the medium was changed. This culturing operation was repeated five times. Yellow colonies of *Thiobacillus thiooxidans* obtained through culturing were isolated, and the isolate was designated as NBI-3.

A reaction vessel of a Warburg manometer equipped with a manometer, a reaction vessel, and a shaker was charged with 5 mg of washed NBI-3 cells, 200 µl of β-alanine-$SO_4^{2-}$ buffer (pH 3.0), and 200 µmol of sodium sulfite, which amount to a total volume of 3 ml. The vessel was further charged with 2 mg of nickel phthalocyanine powders and 2 mg of $W_{28}O_{58}$ powders (Example 1) , 3 mg of nickel phthalocyanine powders and 2 mg of tungsten powders (Example 2), 5 mg of nickel phthalocyanine powders (Comparative Example 1), or nothing as a control (Comparative Example 2). Oxygen uptake of the cells in each sample was measured with the lapse of time, while the pH in the reaction vessel was adjusted to 3.0 with 0.2 ml of sodium hydroxide charged in the center well. The gas phase in the Warburg manometer was maintained at 30° C. with air. The results are shown in FIG. 1.

Figure 1:
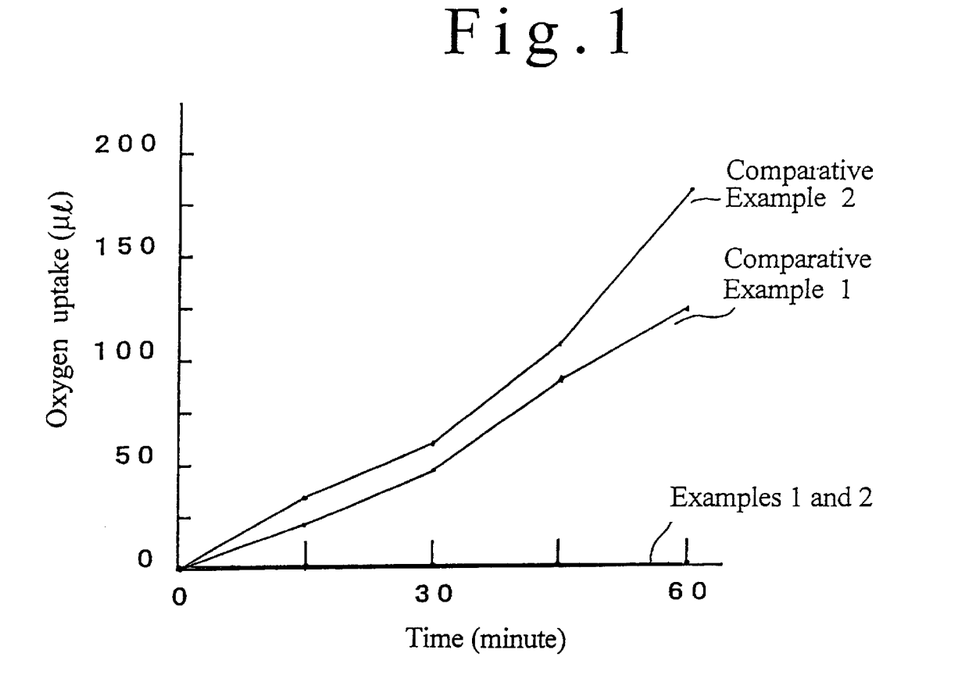
FIG. 1 is a graph showing the oxygen uptake of NBI-3 measured with the lapse of time, comparing the results from each additive used in Examples 1 and 2 and Comparative Examples 1 and 2.

As clearly shown in FIG. 1, absolutely no respiration of the bacteria was observed even at the acidic pH 3 in Examples. Accordingly, it was demonstrated that growth of *Thiobacillus thiooxidans* was inhibited.

Examples 3–4 and Comparative Examples 3–5

A reaction vessel of a Warburg manometer equipped with a manometer, a reaction vessel, and a shaker was charged with 5 mg of washed NBI-3 cells prepared in Example 1, 200 μl of β-alanine-$SO_4^{2-}$ buffer (pH 3.0), and 200 μmol of sodium sulfite, which amount to a total volume of 3 ml. The vessel was further charged with 2 mg of nickel phthalocyanine powders and 2 mg of $W_{28}O_{58}$ powders (Example 3), 2 mg of nickel phthalocyanine powders and 2 mg of tungsten powders (Example 4), 5 mg of $W_{28}O_{58}$ powders (Comparative Example 3), 5 mg of tungsten powders (Comparative Example 4), or nothing as a control (Comparative Example 5). Oxygen uptake of the cells in each sample was measured with the lapse of time, while the pH in the reaction vessel was adjusted to 7.0 with 0.2 ml of sodium hydroxide charged in the center well. The gas phase in the Warburg manometer was maintained at 30° C. with air. The results are shown in FIG. 2.

Figure 2:
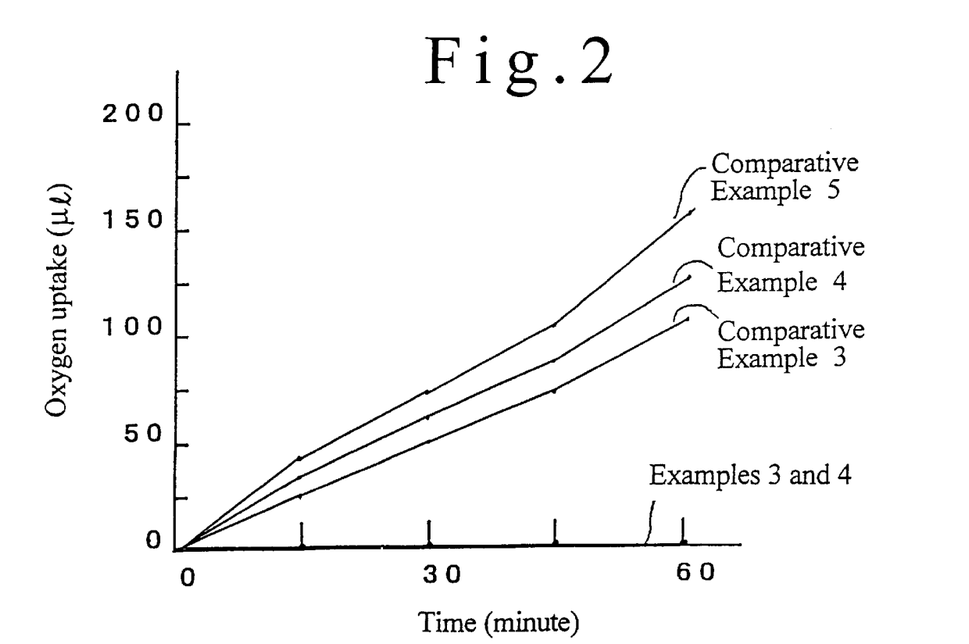
FIG. 2 is a graph showing the oxygen uptake of NBI-3 measured with the lapse of time, comparing the results from each additive used in Examples 3 and 4 and Comparative Examples 3 to 5.

As clearly shown in FIG. 2, absolutely no respiration of the bacteria was observed even at pH 7 in Examples. Accordingly, it was demonstrated that growth of *Thiobacillus thiooxidans* was inhibited.

Examples 5–9 and Comparative Examples 6–9

To a cement composition wherein the ratio of cement : sand was 1:2 by weight and the ratio of water/cement was 1:2 by weight, each *Thiobacillus thiooxidans* growth inhibitor shown in Table 1 was added in an amount shown with respect to 100 parts by weight of cement in Table 1, and a sample of 4×4×16 cm in size was prepared with each resulting mixture. Each sample thus obtained was exposed to the air at the overflow section of a reprocessing sedimentation basin of a sewage treatment facility in a spa area for 6 months. The hydrogen sulfide concentration in the exposure environment was 10 to 30 ppm, the temperature 24 to 32° C., and the humidity 100 %. After the exposure, each sample was cut in the middle, and the sulfur distribution was analyzed by an electron probe micro analyzer. The depth of the area where the sulfur concentration is 0.5 % or higher is measured from the surface of the sample as the sulfur intrusion depth. The results are shown in Table 1.

TABLE 1

| | Kind of *Thiobacillus thiooxidans* growth inhibitor | Amount added*) | Sulfur intrusion depth (mm) |
|---|---|---|---|
| Example 5 | nickel phthalocyanine + W | 0.08 + 0.08 | 0 |
| Example 6 | nickel phthalocyanine + $W_{28}O_{58}$ | 0.1 + 0.1 | 0 |
| Example 7 | nickel phthalocyanine + $WO_3$ | 0.1 + 1.0 | 0 |
| Example 8 | nickel phthalocyanine + $W_{28}O_{58}$ | 0.3 + 0.3 | 0 |
| Example 9 | nickel phthalocyanine + W | 0.3 + 0.3 | 0 |
| Comp. Ex. 6 | W | 0.5 | intruded all through the cross-section |
| Comp. Ex. 7 | $W_{28}O_{58}$ | 0.5 | intruded all through the cross-section |

*)Amount added (parts by weight) based on 100 parts by weight of cement

Referential Example

To each of nickel powders (Ni), tungsten powders (W), $W_{28}O_{58}$ powders, and nickel phthalocyanine powders, a sulfuric acid solution of different pH was added, and the relation between pH and the amount of each metal or metal compound dissolved was measured. The results are shown in FIG. 3.

Figure 3:
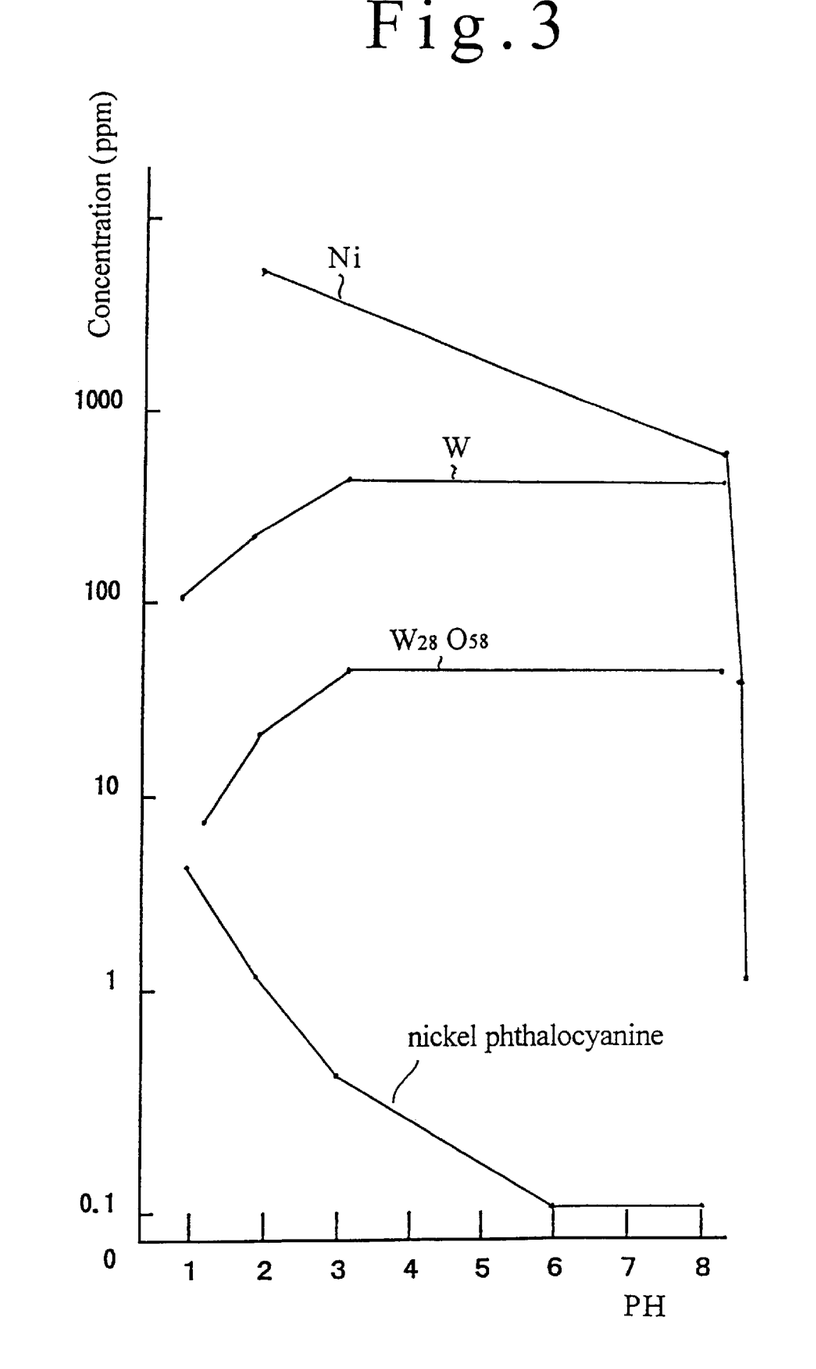
FIG. 3 is a graph illustrating the relation between the pH and the amount of each metal or metal compound dissolved as measured in Referential Example.

It is understood from FIG. 3 that W, $W_{28}O_{58}$, and nickel phthalocyanine hardly dissolved even in the acidic pH range, whereas Ni hardly dissolved around the neutral pH range, but remarkably dissolved in the acidic pH range.

Examples 10–13

To 100 mg of each dispersant shown in Table 2, 10 mg of nickel phthalocyanine powders and 10 mg of powders of each tungsten compound shown in Table 2 were added little by little under agitation, and then dispersed for 2 hours by an attriter filled with zirconia beads of 5 mm diameter, thereby preparing each inhibitor.

Subsequently, to a cement composition wherein the ratio of cement:sand was 1:2 by weight and the ratio of water/cement was 1:2 by weight, each *Thiobacillus thiooxidans* growth inhibitor shown in Table 2 was added in an amount shown with respect to 100 parts by weight of cement in Table 2, and a sample of 4×4×16cm in size was prepared with each resulting mixture. Each sample thus obtained was exposed to the same environment as described in Examples 5–9, and the sulfur intrusion depth in each sample was measured in the same way as in Examples 5–9. The results are shown in Table 2.

TABLE 2

| | Kind of aqueous solution of dispersant in inhibitor | Kind of tungsten compound | Amount added*) | Sulfur intrusion depth (mm) |
|---|---|---|---|---|
| Example 10 | 40% aqueous solution of sodium naphthalene sulfonate | $Na_2WO_4$ | 0.2 | 0 |
| Example 11 | 40% aqueous solution of sodium naphthalene sulfonate | $Na_2WO_4$ | 0.1 | 0 |
| Example 12 | 40% aqueous solution of sodium naphthalene sulfonate | $Ca_2WO_4$ | 0.2 | 0 |
| Example 13 | 50% aqueous solution of triazine-based compound | $Na_2WO_9$ | 0.2 | 0 |

*)Amount added (parts by weight) based on 100 parts by weight of cement

Examples 14–17 and Comparative Example 8

Thiosulfuric acid medium of pH 7.0 was prepared containing 0.50 weight % sodium thiosulfate ($Na_2S_2O_{3.5}H_2O$), 0.15 weight % sodium hydrogenphosphate ($Na_2HPO_{4.12}H_2O$), 1.10 weight % potassium hydrogenphosphate ($KH_2PO_4$), 0.01 weight % magnesium sulfate ($MgSO_{4.7}H_2O$) 0.03 weight % ammonium chloride ($NH_4Cl$), and 0.03 weight % yeast extract.

A sample of 6×6×6mm in size was prepared in the same way as in Examples 10–13, using each inhibitor prepared in Examples 10–13. The sample prepared with the inhibitor of Example 10 was used as Example 14, the sample with the inhibitor of Example 11 as Example 15, the sample with the inhibitor of Example 12 as Example 16, the sample with the inhibitor of Example 13 as Example 17, and the sample with no inhibitor as Comparative Example 8.

Subsequently, each sample was placed in the previously prepared thiosulfuric acid medium, to which NBI-3 prepared in Example 1 was added and cultured at 30° C. for 24 hours.

The amount of calcium dissolved and released from each sample was determined by measuring the change in the amount of calcium ions in the medium at the wave length of 4227 Å using an atomic absorption spectrophotometer (trade name "AA-625-01" manufactured by Shimadzu Corporation). The calcium ion concentration of the standard solution for atomic absorption used here was 1000 μg/ml. The pH of the medium after the culture was 6.0. The results of the measurement on each sample are shown in FIG. 4.

Figure 4:
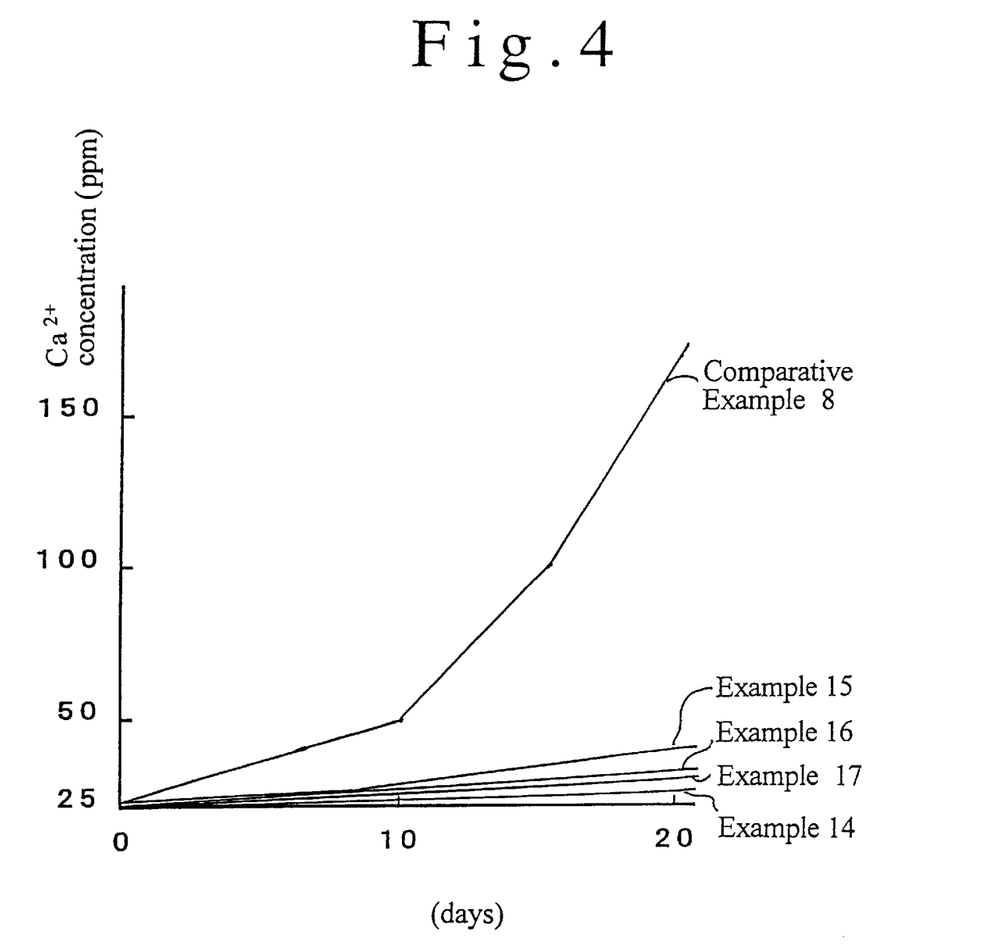
FIG. 4 is a graph showing the amount of released calcium ions measured with the lapse of time when each cement structure is immersed in a culture liquid of NBI-3 in Examples 14 to 17 and Comparative Example 8.

It is understood from the results in FIG. 4 that calcium release was hardly observed from any of the samples of Examples containing the inhibitor of the present invention. Accordingly, it is demonstrated that deterioration of the cement structure was prevented and the metals contained in the inhibitor hardly dissolved.

What is claimed is:

1. A *Thiobacillus thiooxidans* growth inhibitor comprising a first component selected from the group consisting of nickel phthalocyanine powders, powders of a nickel phthalocyanine derivative, and mixtures thereof, and a second component selected from the group consisting of tungsten powders, powders of a substantially water-insoluble tungsten compound, a water-soluble salt of tungstic acid which turns substantially water-insoluble when reacted with cement, and mixtures thereof, said first component being present at a concentration of at least 1 μmol/l and said second component being present at a concentration of at least 1 μmol/l, and wherein when the first component, the second component or both comprise a water-insoluble powder, the cement composition includes an effective amount of dispersant for dispersing the water-insoluble powder in water.

2. The inhibitor of claim 1 wherein said water-insoluble tungsten compound is a member selected from the group consisting of $W_{28}O_{58}$, $WO_3$, calcium tungstate, and mixtures thereof, and the water-soluble salt of tungstic acid is sodium tungstate.

3. The inhibitor of claim 1 further comprising water.

4. The inhibitor of claim 3 wherein said dispersant is selected from the group consisting of salts of naphthalenesulfonic acid, salts of melaminesulfonic acid, salts of ligninsulfonic acid, salts of polycarboxylic acid, polyol, hydroxy carboxylic acid, rhodan compounds, triazine-based compounds, and mixtures thereof.

5. The inhibitor of claim 1, wherein a weight ratio of said first component to said second component is 1: 0.1 to 1: 1.0.

6. The inhibitor of claim 3, wherein said water is contained in 50 to 1000 parts by weight, and said effective amount of the dispersant is 50 to 500 parts by weight, based on 100 parts by weight of said first and second components together.

7. A cement composition comprising:
(a) cement;
(b) aggregates;
(c) water;
(d) a first component selected from the group consisting of nickel phthalocyanine powders, powders of a nickel phthalocyanine derivative, and mixtures thereof; and
(e) a second component selected from the group consisting of tungsten powders, powders of a substantially water-insoluble tungsten compound, a water-soluble salt of tungstic acid which turns substantially water-insoluble when reacted with cement, and mixtures thereof;

when the first component or the second component or both comprise a water-insoluble powder, the cement composition further comprises an effective amount of dispersant for dispersing the water-insoluble powder in water;

said composition being in a fluidized state; the first component comprises 0.0001 to 2 parts by weight based on 100 parts by weight of said cement, and the second component comprises 0.0001 to 2 parts by weight based on 100 parts by weight of said cement.

8. The composition of claim 7 wherein said substantially water-insoluble tungsten compound is selected from the group consisting of $W_{28}O_{58}$, $WO_3$, calcium tungstate, and mixtures thereof; said water-soluble salt of tungstic acid turning to substantially water-insoluble when reacted with cement is sodium tungstate; and said dispersant is selected from the group consisting of salts of naphthalenesulfonic acid, salts of melaminesulfonic acid, salts of ligninsulfonic acid, salts of polycarboxylic acid, polyol, hydroxy carboxylic acid, rhodan compounds, triazine-based compounds, and mixtures thereof.

9. A cement structure obtained by hardening the cement composition of claim 7.

10. The cement composition of claim 7 wherein said water is contained in 20 to 80 parts by weight based on 100 parts by weight of said cement, and said effective amount of the dispersant is 50 to 500 parts by weight based on 100 parts by weight of said first and second components together.

* * * * *

UNITED STATES PATENT AND TRADEMARK OFFICE
CERTIFICATE OF CORRECTION

PATENT NO. : 6,224,658 B1
DATED : May 1, 2001
INVENTOR(S) : Terunobu Maeda et al.

It is certified that error appears in the above-identified patent and that said Letters Patent is hereby corrected as shown below:

<u>Title page,</u>
 Item [73], Assignee, please add:
-- Toyo INK MFG. CO., LTD, Tokyo, Japan --.

Signed and Sealed this

Eighteenth Day of September, 2001

Attest:

NICHOLAS P. GODICI
*Attesting Officer*          *Acting Director of the United States Patent and Trademark Office*